United States Patent [19]

Kousai et al.

[11] Patent Number: 4,778,455
[45] Date of Patent: Oct. 18, 1988

[54] CATHETER

[75] Inventors: Tadashi Kousai; Yousuke Moriuchi; Susumu Tanabe, all of Shizuoka, Japan

[73] Assignee: Terumo Kabushiki Kaisha, Tokyo, Japan

[21] Appl. No.: 137,180

[22] Filed: Dec. 23, 1987

Related U.S. Application Data

[63] Continuation of Ser. No. 828,666, Feb. 12, 1986, abandoned.

[30] Foreign Application Priority Data

Feb. 14, 1985 [JP] Japan ................................. 60-27371

[51] Int. Cl.⁴ ............................................ A61M 25/00
[52] U.S. Cl. ..................................... 604/270; 128/658
[58] Field of Search ................................ 604/264–270, 604/280; 128/656–658

[56] References Cited

U.S. PATENT DOCUMENTS

| 4,182,342 | 1/1980 | Smith | 128/348 |
| 4,410,320 | 10/1983 | Dykstra et al. | 604/27 |
| 4,496,347 | 1/1985 | MacLean et al. | 604/164 |
| 4,516,970 | 5/1985 | Kaufman et al. | 604/270 |
| 4,610,673 | 9/1986 | Russo | 604/270 |

FOREIGN PATENT DOCUMENTS 2533443 3/1984 France.
2065480 7/1981 United Kingdom.

Primary Examiner—Stephen C. Pellegrino
Attorney, Agent, or Firm—Burns, Doane, Swecker & Mathis

[57] ABSTRACT

A nutritive catheter is assembled by attaching a head to the distal end of a main tubing having a duct therethrough, the head being formed from a composition comprising a flexible synthetic resin and a finely divided metal material in a ratio by volume of resin to metal material of at least 2 and having a specific gravity of at least 2. An opening is provided in the head in communication with the tubing duct.

15 Claims, 3 Drawing Sheets

CATHETER

This application is a continuation of application Ser. No. 828,666, filed Feb. 12, 1986 now abandoned.

BACKGROUND OF THE INVENTION

This invention relates to a catheter having a head at its end which is used for administration of nutrient or liquid medicine by orally or nasally inserting it into the digestive tract and indwelling there.

Catheters adapted to be orally or nasally inserted into the digestive tract and indwelled there for feeding nutrient are generally called "nutritive catheters". A suitable leading member is attached to the distal end of a tube which is formed near the distal end with an opening for passage of nutrient fed through the tube duct. There are known in the prior art a variety of such catheters modified so as to facilitate their passage through the esophagus and pylorus, for example, one having a mercury bag at the distal end, one having a metal head at the distal end, and one having metal beads sealed in the tube end (see Japanese Utility Model Application Kokai No. 57-21341, Japanese Utility Model Publication No. 57-44995, and Japanese Utility Model Application Kokai No. 57-36944).

FIG. 2 shows one example of the prior art nutritive catheters in which a head in the form of a bag 5 filled with mercury 6 is attached to the distal end of a main tube 9. The catheter shown in FIG. 3 has a solid metal head 7 attached to the distal end of a main tube 9. A further example of catheter is shown in FIG. 4 as comprising metal beads 8 sealed in the distal end portion of a main tube 9. In all these catheters, an opening 2 for discharging liquid medicine is perforated in the main tube 9.

Attachement of a mercury bag is undesirable in safety because mercury flows out upon breakage or detachment of the bag. A metal head is also dangerous as it can be detached.

In addition, the metal head is difficult to insert as it does not deform in accordance with the insertion path because of hardness. Sealing of metal beads in a tube end is free of such risks as detachment, but requires a more complicated manufacture process with an increased cost.

In all these catheters, the distal end portion of the tube apart from the leading head is formed with a side opening. That portion of the tube where such an opening is present is mechanically weak so that the tube is likely to bend, inviting difficulty of insertion or blockage of flow duct.

There are known some catheters having a radiopaque substance incorporated therein such as lead, barium, bismuth and tungsten compounds. The radiopaque substances usually have a specific gravity of less than 2 and are unsuitable as a weight because they are simply expected to provide contrast effect. Some ferrite-filled materials have a specific gravity of more than 2. Such a high specific gravity is given by incorporating a larger proportion of ferrite. The resulting leading member for a nutritive catheter is too hard to perform as a medical weight requiring flexibility.

SUMMARY OF THE INVENTION

An object of the present invention is to provide a novel and improved nutritive catheter comprising a main tube having attached thereto a leading head which is compatible and flexible so that the head is tightly attached to the main tube whereby the catheter can be readily inserted into the digestive tract without damage to its mucous membrane.

The present invention is directed to a catheter comprising a main tubing having distal and proximal ends and a duct therethrough, a head attached to the distal end of the tubing, and an opening provided near the distal end of the catheter in communication with the duct of the main tubing. According to the present invention, the head is formed from a composition comprising a flexible synthetic resin in admixture with a finely divided metal material. The blend ratio by volume of synthetic resin to metal material is at least 2. The head has a specific gravity of at least 2.

BRIEF DESCRIPTION OF THE DRAWINGS

The objects, features and advantages of the present invention will be more fully understood from the following detailed description when taken in conjunction with the accompanying drawings, in which.

DETAILED DESCRIPTION OF THE INVENTION

Figure 1:
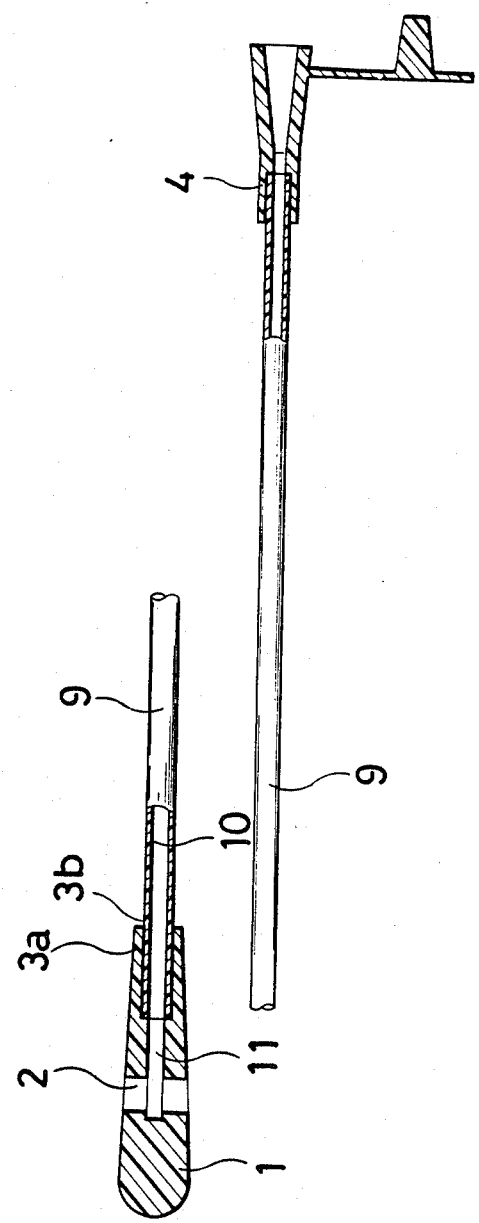
FIG. 1 is a side view, partially in cross section, of a nutritive catheter according to one embodiment of the present invention.
Figure 2:
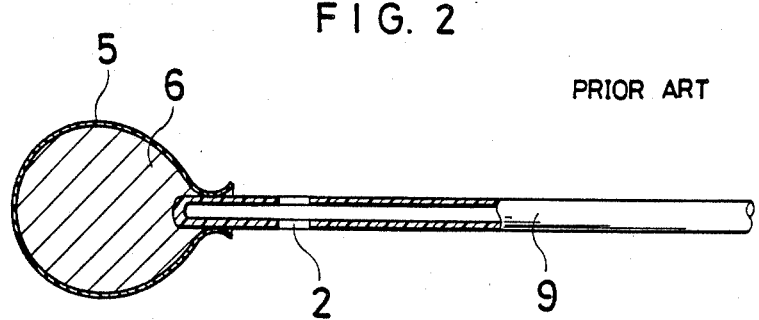
FIGS. 2, 3, and 4 are side views, partially in cross section, of prior art nutritive catheters.
Figure 3:
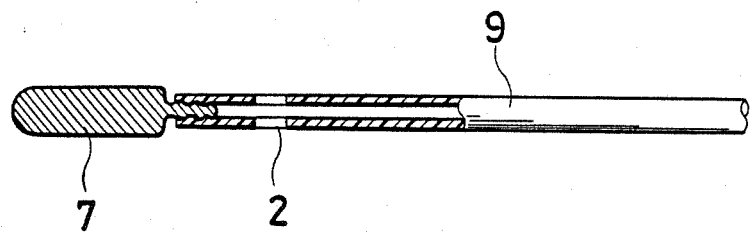
Figure 4:
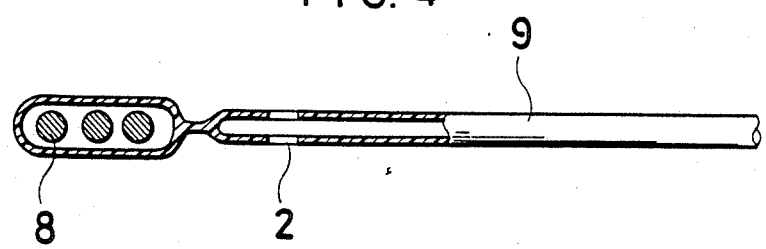

One embodiment of the nutritive catheter according to the present invention is shown in FIG. 1. The nutritive catheter illustrated includes a tube 9 formed of a flexible synthetic resin as a main body. The tube has a duct 10 therethrough and a distal end and a proximal end. A head 1 is fixedly secured to the distal end of the tube 9. The head 1 is formed with at least one opening in the form of a through port 2 for discharging liquid medicine. A connector of the well-known type is fixedly secured to the proximal end of the tube 9. The term liquid medicine used herein includes nutrients as well as ordinary liquid medicines.

Figure 5:
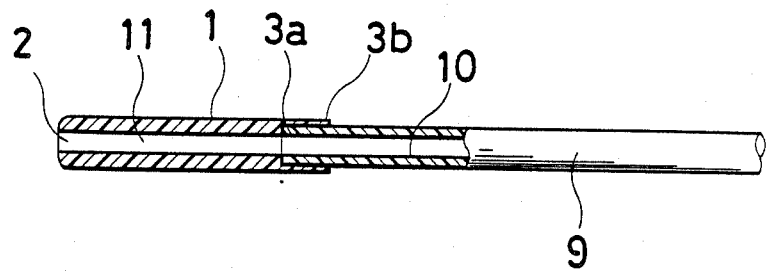
FIGS. 5, 6, and 7 are side views, partially in cross section, of nutritive catheters according to other different embodiments of the present invention.
Figure 6:
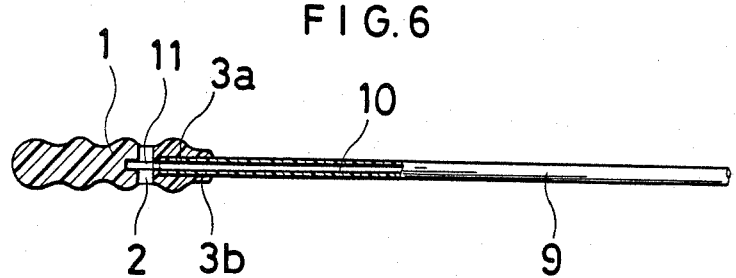
Figure 7:
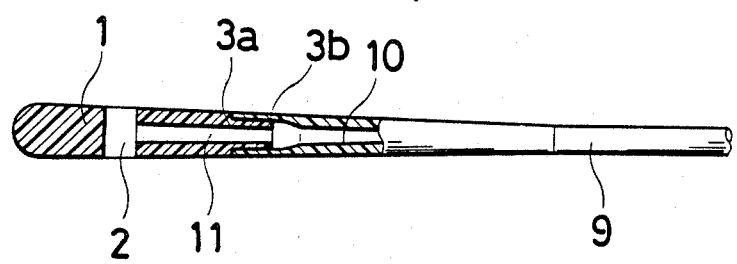

The head 1 can take any shape like bullet shape as shown in FIGS. 1 and 7, cylinder as shown in FIG. 5, and corrugated cylinder as shown in FIG. 6 insofar as it can be orally or nasally inserted into the digestive tract and retained there in a smooth and safe manner. It is preferably shaped to have a rounded leading end in order to facilitate its passage through the esophagus, cardia, and pylorus. The head 1 is formed with at least one opening or through port 2 for discharging liquid medicine and with a bore 11 communicating the port 2 with the duct 10 of the main tube 9. The bore 11 in the head 1 may be a closed bore across which the port 2 extends as shown in FIGS. 1, 6, and 7 or a through bore as shown in FIG. 5. In the structure shown in FIG. 5, the port 2 is given by an opening of the straight through bore 11 at the leading end.

The head 1 is connected to the main tube 9 while a connector portion 3a of the head 1 and a connector portion 3b of the main tube 9 may have approximate inside and outside diameters. More particularly, the head is connected to the main tube 9 in a smooth manner with rather little difference in outside diameter so as to facilitate insertion into the digestive tract. Also, the duct 10 in the tube is smoothly communicated to the bore 11 in the head to faciliate flow of liquid medicine. In the embodiment shown in FIG. 7, the connector portion 3b of the tube 9 is flared to have an increasing diameter while the connector portion 3a of the head 1 is slightly tapered. There is accomplished a head-tube connection having a high bond strength and offering a smooth surface.

The main tube 9 of the nutritive catheter may be formed of any well-known flexible synthetic resins including vinyl chloride resins, polyurethanes, polyethylenes, polyvinyl acetate resins, and silicone resins.

The head 1 may be formed of a composition comprising a known flexible synthetic resin and a finely divided metal material uniformly dispersed therein. The resins include vinyl chloride, urethane, vinyl acetate and silicone resins, but are not limited thereto. The metal materials include metals such as Ti, Cr, Fe, Ni, Bi, W, Pb, Mo, Ta, Hg, Ag, Au and Pt and metal compounds such as $WC$, $WO_2$, $BiO_2$, $(BiO)_2CO_3$, $BaSO_4$, and mixtures thereof. The composition should be formulated so as to have a specific gravity of at least 2, preferably at least 3.

A too larger diameter of the head 1 than the catheter tube 9 makes it difficult to insert the catheter into the digestive tract. Thus, the head 1 preferably has a diameter somewhat larger than the catheter tube 9. The head having a lower specific gravity cannot serve for its own purpose as weight. The specific gravity must be 2 or higher. Higher the specific gravity, the head more performs. The preferred head has a specific gravity of at least 3.

In order that the head 1 of the present invention must have physical properties which are as approximate to those of unloaded flexible synthetic resin as possible while maintaining the specific gravity within the desired range, the blend ratio by volume of flexible synthetic resin to metal material should be at least 2. The resin composition having such a specific blend ratio exhibits not only adequate physical properties including flexibility, but also compatibility with the tube resin composition so that connection between the head and the tube may be readily accomplished by head, high frequency and ultrasonic sealing techniques or by adhesive bonding using solventless adhesives such as epoxy, urethane and rubbery adhesives and solvent adhesives based on tetrahydrofuran (THF), methylethylketone (MEK), and cyclohexanone. Although a heavier composition is advantageous as a weight, incorporating a too larger amount of metal material results in loss of desired physical properties of unloaded resin composition and loss of the feature that molding into any desired shape with a certain degree of softness is possible. It is thus desired that the blend ratio by volume of flexible synthetic resin to metal material be at least 2.

As long as the head 1 according to the present invention has a specific gravity of at least 2 and a resin blend ratio by volume of at least 2, the identity of the flexible synthetic resin and the metal material is not critical. The flexible synthetic resin and the metal material need not necessarily be used alone, and a mixture of two or more may be used for each of them.

In general, flexible synthetic resins are considered as having a specific gravity of approximately 1. When x parts by weight of metal material having a specific gravity d is added to 100 parts by weight of flexible synthetic resin, provided that no mutual dissolution occurs between the flexible synthetic resin and the metal material, the resulting mixture or head formed therefrom has a weight of $(100+x)$ and a volume of $(100+x/d)$. Then the head has a specific gravity of $(100+x)/(100+x/d)$. In order that the specific gravity be 2 or higher, the following equation must be met.

$$(100+x)/(100+x/d) \geq 2 \tag{1}$$

Since the flexible synthetic resin has a volume of approximately 100, the following equation must be met in order that the resin blend volume ratio be 2 or higher.

$$100/x/d \geq 2 \tag{2}$$

Solving equations (1) and (2), then $$d \geq 4.$$

The following equation is also derived from equations (1) and (2).

$$100 \cdot d/(d-2) \leq x \leq 50 \cdot d$$

This gives that
when $d=4$, then $x=200$,
when $d=5$, then $166 \leq x \leq 250$, and
when $d=6$, then $150 \leq x \leq 300$.

Similarly, for tungsten dioxide $WO_2$ having a specific gravity $d=12$, equation (1) gives $x \geq 120$ and equation (2) gives $600 \geq x$. This indicates that a head satisfying the requirements of the present invention may be prepared by blending 120 to 600 parts by weight of $WO_2$ powder to 100 parts by weight of plastic material having a specific gravity of about 1.

For the metal material to be blended with the resinous material having a specific gravity of about 1, there is available a number of combinations of its type in specific gravity and its amount in x parts by weight. The available combinations are encompassed by solid lines in Table 1.

The flexible synthetic resin composition having a specific gravity of about 1 may be formulated in a well-known manner, for example, by blending 80 to 120 parts by weight of a polymer of ethylene, vinyl acetate and carbon monoxide (commercially available under the trade name "Elvaloy" from du Pont) to 100 parts by weight of polyvinyl chloride.

TABLE 1

Specific Gravity of Head Resulting from Various Combinations of Type and Amount of Metal Material Blended with 100 Parts by Weight of Resin Having a Specific Gravity of About 1

| Metal Material Parts by weight | \multicolumn{12}{c}{Specific Gravity d} |
|---|---|---|---|---|---|---|---|---|---|---|---|---|
|  | 1 | 2 | 4 | 6 | 8 | 10 | 12 | 14 | 16 | 18 | 20 | 22 |
| 100  | 1 |     |     | 1.7 |     | 1.8  |      |     |     |     | 1.9 | 1.9  |
| 200  | 1 |     | 2.0 | 2.3 |     |      | 2.6  |     |     |     | 2.7 | 2.75 |
| 300  | 1 | 1.6 |     | 2.7 | 2.9 | 3.1  | 3.2  |     |     |     | 3.5 |      |
| 400  | 1 | 1.7 |     | 3   |     |      | 3.75 |     |     |     | 4.2 |      |
| 500  | 1 | 1.7 | 2.6 | 3.3 |     |      | 4.2  |     |     |     | 4.8 |      |
| 600  | 1 |     | 2.8 |     |     |      |      |     |     |     |     |      |
| 700  | 1 |     | 2.9 | 3.7 |     |      | 5.25 |     |     |     | 5.9 |      |
| 800  | 1 |     | 3.0 |     |     |      |      |     |     |     |     |      |
| 900  | 1 | 1.8 |     |     |     |      |      |     |     |     |     |      |
| 1000 | 1 | 1.8 | 3.1 |     |     |      |      |     |     |     | 7.3 |      |

Table 2 shows examples of the metal materials including metals and metal compounds that can be used to accomplish the combinations encompassed within the solid lines in Table 1.

TABLE 2

Metals and Metal Compounds Specific Gravity Range

| 4–5 | | 5–10 | | 10–15 | | 15–20 | | 20– | |
|---|---|---|---|---|---|---|---|---|---|
| BaSO₄ | 4.5 | Cr | 7.2 | WO₂ | 12.1 | WC | 15.7 | Pt | 21.5 |
| Ti | 4.5 | Fe | 7.86 | Hg | 13.5 | Ta | 16.6 | | |
| | | Bi₂O₃ | 8.76 | Pb | 11.34 | W | 19.3 | | |
| | | Ni | 8.8 | Mo | 10.28 | Au | 19.3 | | |
| | | Bi | 9.8 | Ag | 10.5 | | | | |
| | | (BiO)₂CO₃ | 6.86 | | | | | | |

The head of the present invention may be prepared by blending a variety of metal materials in varying amounts to the resinous materials as mentioned above. When a metal material having a higher specific gravity is used in a smaller amount, the resulting loaded resin composition is more effective as a weight without losing the properties of the flexible synthetic resin. In consideration of some disadvantages of metal material including expensiveness, inconvenient handling, and difficulty in uniform blending with flexible synthetic resin because of high specific gravity, the preferred blends are those of tungsten (W), tungsten dioxide (WO2), tungsten carbide (WC) and mixtures thereof with vinyl chloride and urethane resins. The blending ratio is from 110 to 950 parts by weight of the tungsten material per 100 parts by weight of the resin.

The metal materials blended with the resin preferably have a particle size of 10 μm or less so that they may be uniformly dispersed in the resin to provide a smooth surface. The particularly preferred metal materials have a particle size of 5 μm or less.

The weight, more specifically necessary or optimum weight of the head varies with the diameter (outside and inside diameters) and hardness of the tube to be combined and not limited to a certain range, but must be 0.5 grams or more. More illustratively, for 3Fr tubes having an outside diameter of about 1 mm and an inside diameter of about 0.5 mm, the heads must have a weight of at least about 0.5 grams. Heads having a lighter weight cannot overwhelm the properties of the tube or perform well as a weight, and then the catheter cannot be smoothly advanced against the motion of the stomach and intestine. For 6Fr tubes having an outside diameter of about 2 mm and an inside diameter of about 1.2 mm, the head must have a weight of at least about 1 grams and preferably at least about 1.5 grams. For 8Fr tubes having an outside diameter of about 2.7 mm and an inside diameter of about 1.7 mm, the head must have a weight of at least about 2 grams and preferably at least about 3 grams. For 18Fr tubes having an outside diameter of about 6 mm and an inside diameter of about 4 mm, the head must have a weight of at least about 6 grams.

The size or volume of the head is preferably small because of ease of insertion and indwelling in the human body. More illustratively, the head may desirably have a diameter of less than about 10 mm and a length of less than about 50 mm or a volume of less than about 4 cm³. When a head of such a volume is prepared from a metal-loaded resin composition having the maximum specific gravity of 7.3 in Table 1, it is estimated to have a weight of about 30 grams. This weight value appears to be the upper limit.

The tube is preferably formed of a medically safe material and particularly those plastic materials which are free of plasticizers or contain non-migratory plasticizers when long-term indwelling is intended. The same applies to the resin composition of which the head is formed.

EXAMPLES

In order that those skilled in the art will better understand how to practice the present invention, examples of the present invention are given below by way of illustration and not by way of limitation. All parts are by weight.

EXAMPLE 1

An 8Fr tube having an outside diameter of about 2.7 mm was prepared from a flexible synthetic resin composition of 100 parts by weight of polyvinyl chloride and 100 parts by weight of ethylene-vinyl acetate-carbon monoxide polymer (trade name "Elvaloy" from du Pont). This base resin composition has a specific gravity of about 1.

A loaded bland was prepared by blending 300 parts by weight of tungsten powder having a particle size of 5 μm or less and a specific gravity of about 20 with 100 parts by weight of the same base resin composition. The loaded blend had a blend ratio by volume of resin to tungsten of about 6.7 and a specific gravity of about 3.5. An about 2.2 gram portion of the loaded blend was molded into a head of the shape shown in FIG. 7 having a diameter of 6 mm and a length of 24 mm. The head was bonded to one end of the tube using tetrahydrofuran (THF).

EXAMPLES 2 AND 3

The procedure of Example 1 was repeated except that the base resin compositions from which the tube and the head were formed contained 80 parts (Example 2) and 120 parts (Example 3) of the ethylene-vinyl acetate-carbon monoxide polymer per 100 parts by weight of the polyvinyl chloride.

EXAMPLES 4-6

6Fr tubes having an outside diameter of about 2 mm were prepared from the base resin compositions used in Examples 1-3. The procedure of Examples 1-3 was repeated except that the head had a weight of about 1 gram and was shaped to a diameter of 5 mm and a length of 17 mm.

EXAMPLE 7

An 8Fr tube having an outside diamter of about 2.7 mm was prepared from a vinyl chloride-grafted polyurethane comprising 80% by weight vinyl chloride and 20% by weight polyurethane. This base resin composition had a specific gravity of about 1.2.

A loaded blend was prepared by blending 300 parts by weight of tungsten with 100 parts by weight of the same base resin composition. The loaded blend had a blend ratio by volume of resin to tungsten of about 5.6 and a specific gravity of about 4.1. An about 3 gram portion of the loaded blend was molded into a head of the shape shown in FIG. 7 having a diameter of 6 mm and a length of 28 mm. The head was bonded to one end of the tube using a polyurethane adhesive.

EXAMPLE 8

The procedure of Example 7 was repeated except that the tube was of 6Fr type having an outside diameter of about 2 mm and the head had a weight of about 1.5 grams. The head was shaped to a diameter of 5 mm and a length of 20 mm.

EXAMPLE 9

The procedure of Example 1 was repeated except that the base resin composition from which the tube and the head were formed was polyurethane and bonding was made with cyclohexanone.

EXAMPLE 10

The procedure of Example 1 was repeated except that the base resin composition was a blend of 100 parts by weight of polyvinyl chloride and 60 parts by weight of dioctyl phthalate (DOP) and bonding was made by heat sealing.

EXAMPLE 11

The procedure of Example 1 was repeated except that the loaded blend from which the head was molded was a blend of 100 parts by weight of the base resin composition and 400 parts by weight or iron powder having a specific gravity of 7.86. The loaded blend had a blend ratio by volume of resin to iron of 2 and a specific gravity of 3.3. The head was bonded to the tube with cyclohexane. The head weighed 2.1 grams.

EXAMPLE 12

The procedure of Example 1 was repeated except that the loaded blend from which the head was molded was a blend of 100 parts by weight of the base resin composition and 400 parts by weight of $WO_2$ powder having a specific gravity of 12.1. The loaded blend had a blend ratio by volume of resin to tungsten dioxide and 3 and a specific gravity of 3.8. The head weighed 2.4 grams.

COMPARATIVE EXAMPLE 1

An 8Fr tube was prepared using the base resin composition from Example 1.

A loaded blend was prepared by blending 600 parts by weight of iron powder with 100 parts by weight of the same base resin composition. The loaded blend had a blend ratio by volume of resin to iron of about 1.3 and a specific gravity of about 4.0. A head weighing 2.5 grams was molded from the loaded blend. The head was bonded to one end of the tube using THF.

COMPARATIVE EXAMPLE 2

An 8Fr tube was prepared using the base resin composition from Example 1.

A loaded blend was prepared by blending 95 parts by weight of titanium powder with 100 parts by weight of the same base resin composition. The loaded blend had a blend ratio by volume of resin to titanium of about 4.5 and a specific gravity of about 1.6. A head weighing 1.0 gram was molded from the loaded blend. The head was bonded to one end of the tube using THF.

In all the examples, the catheter heads were flexible enough to be readily inserted without damage to the mucous membrane upon treatment of patients and fully functioned as a weight. Neither tube bending nor head detachment occurred because of the presence of a discharge port in the head and great bond strength between the head and the tube. Particularly, those heads having a volume blend ratio of resin to metal material of at least 3 were more effective to prevent damage to the mucous membrane and easy to insert into the body.

On the contrary, the catheter head of Comparative Example 1 had a satisfactory weight, but was too hard to function as a leading weight. The catheter could not be clinically used because it was expected to probably damage the nasal mucosa upon insertion through nasal cavity. It could not be used in practice because the bond strength between the head and the tube was too low to prevent the head from being readily detached.

The catheter head of Comparative Example 2 was flexible enough to eliminate the danger of mucosa damage, but its weight of 1 gram was too light as a weight for the 8Fr catheter. The catheter could not be used because such a light head was expected to be unsuccessful as a weight in smoothly leading the catheter under the motion of the stomach and intestine.

BENEFITS OF THE INVENTION

The nutritive catheter of the present invention has a head molded from a flexible synthetic resin composition of a flexible synthetic resin and a finely divided metal material uniformly disposed therein, that is, a flexible loaded resin composition having a high specific gravity of at least 2. The head is sufficiently heavy as a leading weight because of its high specific gravity and can be readily advanced through the digestive tract without mucosal damage because of its flexibility.

The head molded from the flexible synthetic resin having finely divided metal material loaded is sufficiently elastic and flexible to readily restore to the original shape even when deformed so that it can be easily inserted into the body treat. The opening formed in the head would not be blocked even when the head is deformed, ensuring continuous passage of liquid medicine.

The head has properties essentially similar to those of the resin material so that it can be readily and firmly bonded to the main body by any suitable bonding techniques as by adhesive bonding or high-frequency sealing or ultrasonic sealing. There is no likelihood that the head be detached from the main tube. This leads to advantages in safety and production.

The provision of a liquid discharge opening in the head itself avoids bending of the main tube.

When the head is connected to the flared distal end of the main tube having an increasing diameter, the bond strength between the head and the tube is enhanced to essentially avoid bending of the tube in that region.

The provision of an opening in the head leading end defines a straight bore through which liquid medicine passes so that clogging of liquid medicine scarecely occurs as compared with openings formed in the side wall of the head or tube.

We claim:

1. A catheter comprising
   a main tubing having distal and proximal ends and a duct therethrough,
   a head attached to the distal end of the tubing, and
   an opening provided near the distal end of the catheter in communication with the duct of the main tubing, characterized in that
   said head is formed from a composition comprising a flexible synthetic resin in admixture with a finely divided metal material, with the blend ratio by volume of synthetic resin to metal material being at least 2, and has a specific gravity of at least 2, wherein said finely divided metal material has a particle size of up to 10 $\mu$m.

2. The catheter of claim 1 wherein said head has a specific gravity of at least 3.

3. The catheter of claim 2 wherein said synthetic resin is selected from the group consisting of vinyl chloride resins, urethane resins, silicone resins, polyethylene, and vinyl acetate resins.

4. The catheter of claim 2 wherein said metal material is selected from a metal, a metal compound, and mixtures thereof.

5. The catheter of claim 2 wherein said metal material is at least one member selected from the group consisting of tungsten, tungsten dioxide, and tungsten carbide.

6. The catheter of claim 1 wherein said opening is formed in said head.

7. The catheter of claim 6 wherein said opening is formed in the free end of said head.

8. The catheter of claim 1 wherein said finely divided metal material is a powdery metal material.

9. The catheter of claim 1 wherein said finely divided metal material has a particle size of up to 10 $\mu$m.

10. The catheter of claim 9 wherein said finely divided metal material has a particle size of up to 5 $\mu$m.

11. The catheter of claim 1 wherein said synthetic resin is selected from the group consisting of vinyl chloride resins, urethane resins, silicone resins, polyethylene, and vinyl acetate resins.

12. The catheter of claim 1 wherein said metal material is selected from a metal, a metal compound, and mixtures thereof.

13. The catheter of claim 1 wherein said metal material is at least one member selected from the group consisting of tungsten, tungsten dioxide, and tungsten carbide.

14. The catheter of claim 1 wherein said head is a bullet-shaped body having a rounded leading edge and a trailing edge adjacent said distal end, said body having an axially extending bore, said bore being in fluid communication with said duct and extending to an intermediate portion of said body to form said opening.

15. The catheter of claim 14 wherein said axially extended bore comprises a first portion coaxial with the duct and a second portion essentially traversing said first portion at the distal end thereof to form said opening.

* * * * *